United States Patent
Thornton et al.

(10) Patent No.: US 7,332,268 B2
(45) Date of Patent: Feb. 19, 2008

(54) LAYERED SUPPORT SHEET FOR HIGH-YIELD SPOT CUTTING FROM GELS OR MEMBRANES

(75) Inventors: Kevin Thornton, Fairfield, CA (US); Randy Gordon-Gilmore, Rio Vista, CA (US); Dan McEachern, Alameda, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 126 days.

(21) Appl. No.: 11/400,167

(22) Filed: Apr. 6, 2006

(65) Prior Publication Data

US 2006/0246419 A1   Nov. 2, 2006

Related U.S. Application Data

(60) Provisional application No. 60/669,453, filed on Apr. 7, 2005.

(51) Int. Cl.
*C12Q 1/00* (2006.01)
*B26F 1/00* (2006.01)

(52) U.S. Cl. ............... 435/4; 30/358; 30/360; 204/462

(58) Field of Classification Search .......... None
See application file for complete search history.

(56) References Cited

U.S. PATENT DOCUMENTS 3,482,311 A * 12/1969 Farris .................. 30/358
3,954,033 A * 5/1976 Tipton et al. .......... 83/51
5,100,709 A    3/1992 Barger et al.
5,693,405 A   12/1997 Harvie et al.
5,993,627 A * 11/1999 Anderson et al. ........ 204/456
6,398,932 B1   6/2002 Anderson et al.
6,808,665 B1  10/2004 Percival
6,974,528 B2 * 12/2005 Liu et al. .............. 204/456
2006/0029574 A1*  2/2006 Albitar et al. .......... 424/93.1
2006/0094062 A1*  5/2006 Wu et al. .............. 435/7.1
2006/0245839 A1* 11/2006 Price et al. ............ 409/185

FOREIGN PATENT DOCUMENTS

JP        2005069905      *  3/2005
WO     WO 99/15875 A1       4/1999
WO     WO 00/57153 A1       9/2000

OTHER PUBLICATIONS

"Proteomics Core Facility: Instrumentation"; 2005, http://proteomics.ctrl.ucla.edu/public/instrumentation.adp, 3 pages.
"ProteomeWorks Spot Cutter System"; 2005, South Dakota Biomedical Research Infrastructure Network, http://www.usd.edu/brin/text/resources/spotcutter.htm, 2 pages.

* cited by examiner

*Primary Examiner*—Christopher R. Tate
(74) *Attorney, Agent, or Firm*—Townsend and Townsend and Crew LLP; M. Henry Heines

(57) ABSTRACT

The excision of sample spots from a gel or membrane by pressing a cutting tool terminating in a hollow cylinder against the gel or membrane supported on a rigid surface is made more reliable by interposing a relatively pliable, intermediate layer on the side of the surface facing the gel or membrane. The pliability of the intermediate layer compensates for any irregularity or misalignment of the cutting edge of the cylinder relative to the gel or membrane.

10 Claims, 1 Drawing Sheet

LAYERED SUPPORT SHEET FOR HIGH-YIELD SPOT CUTTING FROM GELS OR MEMBRANES

CROSS-REFERENCE TO RELATED APPLICATION

This application claims benefit from U.S. Provisional Patent Application No. 60/669,453, filed Apr. 7, 2005, the contents of which are incorporated herein by reference in their entirety.

BACKGROUND OF THE INVENTION

1. Field of the Invention

This invention resides in the field of biochemical laboratory equipment, and particularly equipment that is used for analyses of multitudes of small samples of biologically derived materials.

2. Description of the Prior Art

Many biochemical laboratories perform procedures that involve analyses of large numbers of samples, each containing biological species that are very similar in structure and each available only in very small quantities. Analyses of this kind are performed in a sequence of stages, each stage requiring close control of the reaction conditions while maintaining individual handling of each sample. To accomplish this, the samples are often arranged in two-dimensional arrays, and sophisticated instrumentation, frequently involving robotics, is used to remove individual samples from an array and transport the samples to various stations where the different stages of the procedure are performed. Proteomics is an example of such a procedure. The species to be isolated in proteomics typically reside in spots on a two-dimensional gel or on a membrane to which the spots have been transferred from a gel. Polyvinylidene difluoride (PVDF) and nitrocellulose are examples of materials from which such membranes are made. The individual stages in a proteomics procedure include imaging of the array and location of the spots, plus excision of the spots from the array, transfer of the excised spots to various locations, digestion of the substances contained in the spots, and analysis of the digested substances, all performed by the instrument under computer control. The digestion and analysis steps are typically performed in the wells of a multi-well plate such as a 96-well microplate, and excision of the spots from the membrane and transfer to the wells are performed by an automated spot cutter which is controlled by the robotics.

The typical spot cutter includes a cutting tool that terminates in a hollow cylinder that is approximately the size of a hypodermic needle. The tool is movable in the x-y plane for positioning over individual spots, and in the z-direction to be lowered onto the gel or membrane to cut a very small disk containing the spot from the gel or membrane. Disclosures of robotics-containing instrumentation for performing this task are found in International Patent Publication No. WO 99/15875, MacQuarie Research Ltd., applicant, publication date 1 Apr. 1999 ("Apparatus for Removing a Sample From an Array of Samples and a Cutting Tool for Use With That Apparatus"), and in International Patent Publication No. WO 00/57153, Campbell Corporation Pty. Ltd., applicant, publication date 28 Sep. 2000 ("Improvements in Apparatus and Method for Removing Samples"). An example of instrumentation that incorporates disk-excising robotics is the 2DiD integrated system for imaging and spot-picking of LEAP Technologies (Carrboro, N.C., USA). Other examples of spot cutters for use in proteomics are the ProteomeWorks™ Plus Spot Cutter and the EXQuest™ Spot Cutter, both of Bio-Rad Laboratories, Inc., Hercules, Calif., USA.

To facilitate the cutting operation, the gel or membrane is placed on a rigid surface, such as that of a polycarbonate sheet, and the cutting tool is lowered onto and pressed against the surface, causing the cylinder to cut through the gel or membrane to remove a spot in the shape of a disk the size of the cylinder interior. A risk in this operation is that the cutting of the spot may be incomplete, thereby preventing the spot from being fully liberated from the remainder of the gel or membrane. This can occur when the cylinder is not exactly perpendicular to the rigid surface underlying the gel or membrane. A lack of perpendicularity can also cause a partially cut piece to be pulled out of the cylinder tip as the cutting tool is being lifted away. Even if full separation is achieved, an angled cylinder can also cause the cut piece to enter the cylinder at an angle that might interfere with the proper ejection of the piece or that might prevent ejection entirely. Another risk in this procedure is that the cutting edge may scratch the support surface. This can compromise the reliability of the operation for subsequent gels or membranes.

SUMMARY OF THE INVENTION

It has now been discovered that these problems and others in connection with spot cutting can be reduced or eliminated by using a support surface covered with a thin, relatively soft, layer, i.e., one that is softer (more pliable) than the underlying support surface, on the side facing the gel or membrane. This intermediate layer is not part of the gel or membrane and is sufficiently pliable to compensate for any irregularity in, or misalignment of, the cutting edge of the cutting tool relative to the gel or membrane. The tool is thus lowered against the gel or membrane and pressed with sufficient force to penetrate the gel or membrane without penetrating the intermediate layer, thereby fully excising the spot in the form of a disk from the gel or membrane without also excising any of the intermediate layer. The intermediate layer is preferably adhered to the underlying support surface and, and the intermediate layer can be either removable from or permanently affixed to the surface. The presence of the intermediate layer allows the cutting tool to safely and completely cut a spot and remove the cut spot from the gel or membrane without scratching or otherwise damaging the surface, and with at most a temporary depression in the intermediate layer. The presence of the intermediate layer also allows the use of a cutting tool terminating in a cylinder that has a blunt cutting edge, in addition to tools terminating in cylinders that have sharp cutting edges.

DETAILED DESCRIPTION OF THE INVENTION AND PREFERRED EMBODIMENTS

Figure 1:
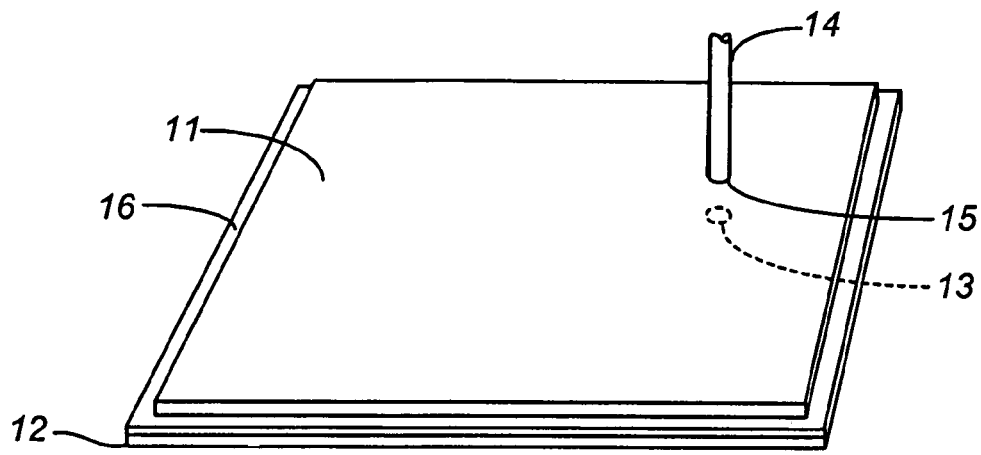
FIG. 1 is a perspective view of a gel, support plate, and intermediate layer, with a cutting tool poised above the gel for use in the practice of the prevention.

The term "sheet-form matrix" is used in this specification and the appended claims as a generic term to denote the medium in which the sample array resides. Gels and membranes are both encompassed by the term. The "cylinder" cited in this specification and the appended claims is any body formed by a line tracing a closed curve. The closed curve may thus for example be a square, a rectangle, or other polygon, or an ellipse or a circle. Circles and hence circular cylinders are preferred.

The support surface can be formed of any conventional material that is commonly used in laboratory equipment and in parts and components for laboratory instrumentation. By "rigid surface" is meant a surface having sufficient rigidity to support the sheet-form matrix, whether it be a gel or a membrane, in a substantially flat configuration. The rigid surface can therefore be the surface of a sheet that is moderately flexible. A convenient material for the support surface is a polymer such as polycarbonate, although other polymers that are equally suitable will be readily apparent to the manufacturer of such equipment and can be used as well. Among the alternatives to polycarbonate are poly(methyl methacrylate), polyurethanes, polyesters, polyamides, polyimides, phenolic resins, cellulosic resins, polystyrene, styrene copolymers, and polyethylene terephthalate.

The term "intermediate layer" is used herein to denote the pliable layer interposed between the rigid surface and the sheet-form matrix. The intermediate layer is a relatively soft and pliable polymeric material. Examples are polyethylene, polypropylene, poly(methyl methacrylate), silicones, polyesters, poly(vinyl chloride), poly(vinyl dichloride), and polyvinyl alcohol and various copolymers and other formulated polymers. Polyethylene, particularly low-density polyethylene, polypropylene, poly(vinyl chloride), poly(vinyl dichloride), and polyvinyl alcohol are preferred. The thickness of the intermediate layer may vary as well. In most cases, best results will be obtained with a thickness of from about 0.001 cm to about 0.01 cm, and in a presently preferred embodiment, the thickness of about 0.0025 cm. When both the underlying plate and the intermediate layer are polymers, the rigidity or pliability (i.e., softness) of each can be controlled by selection of the monomer(s) from which each is formed, the molecular weight of the polymer, the degree of crosslinking of the polymer, the inclusion of additives, and any other factors known in polymer chemistry to affect the physical characteristics of the material. A quick-release coating can also be present between the rigid support surface and the intermediate layer to enable the intermediate layer to be removed and replaced. Examples of quick-release coatings are silanes, silicones, siloxane, acrylic resins, and polytetrafluoroethylene. This invention contemplates the use of intermediate layers that removable as well as those that are not removable.

Plates covered with protective films that are designed for use in the graphic arts industry and in graphic arts products, where the films serve as masking layers, can be used in the practice of the present invention. In graphic arts applications, the masking layer is typically removed prior to use of the underlying plate. The same plate and masking layer can be used in the practice of the present invention by retaining the masking layer rather than removing it, and placing the sheet-form matrix over the masking layer, the masking layer thereby serving as the intermediate layer. In one example of the practice of this invention, the underlying, relatively rigid film can be formed of LEXAN® 8010, a polycarbonate film 0.010 inch (0.0254 cm) in thickness covered by a masking layer of polyethylene approximately 0.001 inch (0.0025 cm) in thickness. This product is sold by GE Plastics, Fairfield, Conn., USA. Disclosures of this type of product and the compositions of its layers are found in U.S. Pat. No. 5,100,709 (Barger, D. D., et al., issued Mar. 31, 1992), U.S. Pat. No. 5,693,405 (Harvie, W. E., et al., issued Dec. 2, 1997), and U.S. Pat. No. 6,808,665 B1 (Percival, J. D., issued Oct. 26, 2004). The full disclosures of these patents and all other patents and publications cited in this specification are hereby incorporated herein by reference.

The relatively soft intermediate layer of this invention can be used with any gel or membrane that is commonly used or known to be usable in biochemical separations, particularly two-dimensional electrophoretic separations. Gels with a surface skin, such as polyacrylamide gels, are of particular interest since force is required to penetrate the skin and liberate the spot from the remainder of the gel, and the thin soft layer over the support surface offers enough resistance despite its resiliency to allow force to be applied to the gel without harm to the surface. The invention can be used with other gels as well, such as agarose gels.

The figures hereto depict one example of an implementation of the present invention. The perspective view of FIG. 1 shows a gel 11 placed on the top surface of a flat rigid plate 12 to keep the gel flat while a section is removed from the gel. The gel contains a two-dimensional array of sample spots of which only one 13 is shown. Poised above the spot 13 and ready to be lowered onto the spot is a cutting tool 14 of which only the hollow cylinder is shown, the tool having an open lower end that terminates in a cutting edge 15. The upper surface of the rigid plate 12 is covered with a pliable film 16 (the intermediate layer) which is more readily seen in the cross sections of FIGS. 2 and 3.

Figure 2:
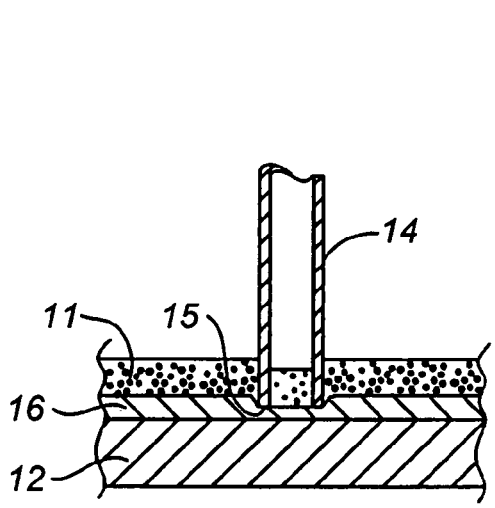
FIG. 2 is a cross section of the components shown in FIG. 1 in the process of excising a sample from the gel.
Figure 3:
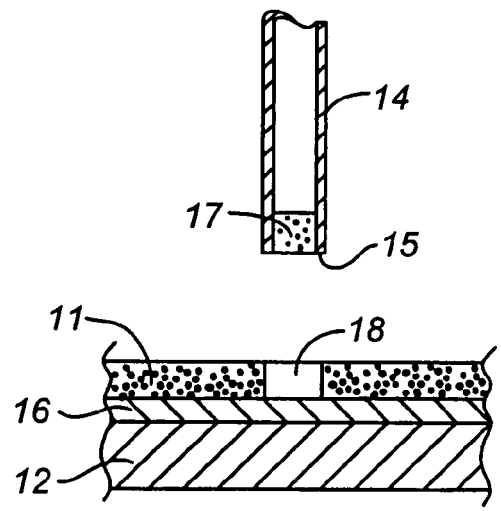
FIG. 3 is the same cross section view as FIG. 2 with the excision of the sample from the gel completed.

FIGS. 2 and 3 show the cutting tool 14 in two different positions, respectively. In FIG. 2, the tool 14 has been pressed into the gel 11, penetrating the gel and contacting the pliable film 16, making a temporary depression in the film. In FIG. 3, the tool 14 has been lifted from the plate 12 and film 16, with the disk 17 that has been excised from the gel retained inside the hollow cylinder of the tool, leaving a hole 18 in the gel at the location from which the disk 17 was cut. This excised disk 17 can now be transported with the cutting tool 14 to another station of the analytical instrument, where the disk 17 can be ejected from the tool 14 by conventional means, such as air or hydraulic pressure, vacuum, dissolving, or a mechanical ram.

The foregoing is offered primarily for purposes of illustration. Variations in the shapes and arrangements of the various components that still incorporate the basic elements of this invention, as expressed in the appended claims, will be readily apparent to those skilled in the art of laboratory equipment and its design, construction, and use.

In the appended claims, the terms "comprise," "comprises," and "comprising" all denote the inclusion of the element, component, or step, or group of elements, components, or steps, that follow the term, but not the exclusion of any other element, component or step not expressly stated. Likewise, the terms "a" and "an" denote "one or more."

What is claimed is:

1. In a method for excising a section from a sheet-form matrix on which are deposited a spatial array of samples of biologically derived materials, said method comprising placing said matrix on a rigid surface and pressing a hollow cylinder with an open end against said matrix and said rigid surface, the improvement comprising interposing between said matrix and said rigid surface an intermediate layer of pliable polymeric material and pressing said hollow cylinder against said matrix, said intermediate layer, and said rigid surface in a manner causing said hollow cylinder to penetrate said matrix and contact said intermediate layer without penetrating said intermediate layer.

2. The method of claim 1 wherein said intermediate layer is a film of a member selected from the group consisting of polyethylene, polypropylene, poly(vinyl chloride), poly(vinyl dichloride), and polyvinyl alcohol.

3. The method of claim 1 wherein said intermediate layer is a film of polyethylene.

4. The method of claim 1 wherein said intermediate layer is a film having a thickness of from about 0.001 cm to about 0.01 cm.

5. The method of claim 1 wherein said intermediate layer is a film having a thickness of approximately 0.0025 cm.

6. The method of claim 1 wherein said intermediate layer is a film of low-density polyethylene.

7. The method of claim 1 wherein said rigid surface is a surface of a polycarbonate sheet.

8. The method of claim 1 wherein said intermediate layer is adherent to said surface yet removable therefrom.

9. The method of claim 1 wherein said hollow cylinder has a blunt cutting edge.

10. The method of claim 1 wherein said hollow cylinder has a sharp cutting edge.

* * * * *